(12) United States Patent
Nagaoka (10) Patent No.: US 9,581,803 B2
(45) Date of Patent: Feb. 28, 2017

(54) OBSERVATION APPARATUS

(71) Applicant: OLYMPUS CORPORATION, Hachioji-shi, Tokyo (JP)

(72) Inventor: Hideyuki Nagaoka, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/205,752

(22) Filed: Jul. 8, 2016

(65) Prior Publication Data
US 2016/0320607 A1  Nov. 3, 2016

Related U.S. Application Data

(63) Continuation of application No. PCT/JP2015/072970, filed on Aug. 14, 2015.

(30) Foreign Application Priority Data

Aug. 20, 2014 (JP) ................................ 2014-167434

(51) Int. Cl.
  *H04N 5/00* (2011.01)
  *G02B 23/24* (2006.01)
  (Continued)

(52) U.S. Cl.
  CPC ..... *G02B 23/2461* (2013.01); *G02B 23/2484* (2013.01); *H04N 5/2256* (2013.01); *H04N 5/232* (2013.01); *H04N 9/04* (2013.01)

(58) Field of Classification Search
  CPC  H05B 33/08; H05B 33/0848; H05B 33/0818; H05B 33/0872; H05B 33/0869; H05B 33/0803; H05B 37/02
  See application file for complete search history.

(56) References Cited

U.S. PATENT DOCUMENTS 8,159,150 B2 * 4/2012 Ashdown ........... H05B 33/0818
                                                       315/149
9,345,097 B1 * 5/2016 Ho ..................... H05B 33/0818
(Continued)

FOREIGN PATENT DOCUMENTS

JP  2003093335 A  4/2003
JP  2005227426 A  8/2005
(Continued)

OTHER PUBLICATIONS

International Search Report (ISR) dated Oct. 27, 2015 issued in International Application No. PCT/JP2015/072970.

*Primary Examiner* — Frank Huang
(74) *Attorney, Agent, or Firm* — Holtz, Holtz & Volek PC (57) ABSTRACT

An observation apparatus including: a light source unit that generates illumination light by using a plurality of solid-state illumination devices; an image-acquisition device that acquires an image of an object illuminated with the illumination light; an image processing unit that processes acquired image signals; and a control unit that controls the light source unit and/or the image processing unit. One of the illumination devices has a peak in a G channel, another one of the illumination devices has a peak in an R channel, and, when increasing and reducing the amount of the illumination light, the control unit performs control so as to satisfy $\Delta Sr/\Delta Sg>1$ and $\Delta Sr/\Delta Sg<1$, respectively, where $\Delta Sr$ and $\Delta Sg$ are rates of change of system gains applied to the R and G channels, respectively.

9 Claims, 8 Drawing Sheets

(51) Int. Cl.
*H04N 5/225* (2006.01)
*H04N 5/232* (2006.01)
*H04N 9/04* (2006.01)

(56) References Cited

U.S. PATENT DOCUMENTS

| | | | |
|---|---|---|---|
| 2003/0060684 A1* | 3/2003 | Ayame | A61B 1/00096 600/181 |
| 2009/0156901 A1* | 6/2009 | Gono | A61B 1/0646 600/180 |
| 2009/0278920 A1 | 11/2009 | Kamo | |
| 2010/0182294 A1* | 7/2010 | Roshan | G01J 1/32 345/207 |
| 2011/0133654 A1* | 6/2011 | McKenzie | F21K 9/00 315/152 |
| 2016/0066384 A1* | 3/2016 | Dias | H05B 33/0848 315/152 |

FOREIGN PATENT DOCUMENTS

| | | | |
|---|---|---|---|
| JP | 2007097649 A | 4/2007 |
| JP | 2007279632 A | 10/2007 |
| JP | 2008058387 A | 3/2008 |
| JP | 2009276371 A | 11/2009 |
| JP | 2010158415 A | 7/2010 |
| JP | 2012170488 A | 9/2012 |
| JP | 2012217486 A | 11/2012 |

* cited by examiner

| IDENTIFICATION INFORMATION \ TARGET CURRENT SUPPLY AMOUNT mA | CURRENT-SUPPLY-AMOUNT RATIO | | | | | | | | | | | |
|---|---|---|---|---|---|---|---|---|---|---|---|---|
| | 100 | | | 200 | | | 300 | | | 400 | | |
| | R | G | B | R | G | B | R | G | B | R | G | B |
| A | 2 | 1 | 3 | 2.1 | 1 | 3.1 | 2.2 | 1 | 3.2 | 2.3 | 1 | 3.3 |
| B | ⋯ | | | | | | | | | | | |
| C | ⋯ | | | | | | | | | | | |
| D | ⋯ | | | | | | | | | | | |

| IDENTIFICATION INFORMATION | CURRENT-SUPPLY-AMOUNT RATIO | | |
|---|---|---|---|
| | R | G | B |
| A | 2 | 1 | 3 |
| B | ...... | | |
| C | ...... | | |
| D | ...... | | |

FIG. 6

| IDENTIFICATION INFORMATION | IMAGE PROCESSING GAIN | | |
|---|---|---|---|
| | R | G | B |
| A | 1.05 | 1 | 1.03 |
| B | ...... | | |
| C | ...... | | |
| D | ...... | | |

FIG. 7

| IDENTIFICATION INFORMATION | WHITE BALANCE GAIN | | |
|---|---|---|---|
| | R | G | B |
| A | 1.05 | 1 | 1.03 |
| B | ...... | | |
| C | ...... | | |
| D | ...... | | |

| TARGET CURRENT SUPPLY AMOUNT mA / IDENTIFICATION INFORMATION | IMAGE PROCESSING GAIN | | | | | | | | | | | |
|---|---|---|---|---|---|---|---|---|---|---|---|---|
| | 100 | | | 200 | | | 300 | | | 400 | | |
| | R | G | B | R | G | B | R | G | B | R | G | B |
| A | 1 | 1 | 1 | 1.05 | 1 | 1.03 | 1.1 | 1 | 1.07 | 1.2 | 1 | 1.11 |
| B | ⋮ | | | | | | | | | | | |
| C | ⋮ | | | | | | | | | | | |
| D | ⋮ | | | | | | | | | | | |

FIG. 10

| IDENTIFICATION INFORMATION \ TARGET CURRENT SUPPLY AMOUNT mA | WHITE BALANCE GAIN | | | | | | | | | | | |
|---|---|---|---|---|---|---|---|---|---|---|---|---|
| | 100 | | | 200 | | | 300 | | | 400 | | |
| | R | G | B | R | G | B | R | G | B | R | G | B |
| A | 1 | 1 | 1 | 1.05 | 1 | 1.03 | 1.1 | 1 | 1.07 | 1.2 | 1 | 1.11 |
| B | ⋯ | | | | | | | | | | | |
| C | ⋯ | | | | | | | | | | | |
| D | ⋯ | | | | | | | | | | | |

OBSERVATION APPARATUS

CROSS-REFERENCE TO RELATED APPLICATIONS

This is a continuation of International Application PCT/JP2015/072970, with an international filing date of Aug. 14, 2015, which is hereby incorporated by reference herein in its entirety. This application claims the benefit of Japanese Patent Application No. 2014-167434, filed on Aug. 20, 2014, the content of which is incorporated herein by reference.

Technical Field

The present invention relates to observation apparatuses.

Background Art

A known observation apparatus in the related art adjusts the balance among R light, G light, and B light to prevent the color of an observation image from changing as a result of the proportions of the R light, the G light, and the B light contained in illumination light changing due to the individual differences among LEDs when the amount of current supply is increased or decreased (for example, see PTL 1).

CITATION LIST

Patent Literature

{PTL 1}Japanese Unexamined Patent Application, Publication No. 2012-217486

SUMMARY OF INVENTION

According to an aspect of the present invention, there is provided an observation apparatus including: a light source unit that generates illumination light by using a plurality of solid-state illumination devices; an image-acquisition device that acquires an image of an object illuminated with the illumination light generated by the light source unit; an image processing unit that processes image signals acquired by the image-acquisition device; and a control unit that controls at least one of the light source unit and the image processing unit. At least one of the solid-state illumination devices of the light source unit has a peak in a G channel, at least another one of the solid-state illumination devices of the light source unit has a peak in an R channel, and, when the control unit increases the amount of the illumination light emitted from the light source unit, the control unit performs control so as to satisfy Conditional Expression (1), and, when the control unit reduces the amount of the illumination light emitted from the light source unit, the control unit performs control so as to satisfy Conditional Expression (2):

$$\Delta Sr/\Delta Sg > 1 \quad (1)$$

$$\Delta Sr/\Delta Sg < 1 \quad (2)$$

where $\Delta Sr$ is a rate of change of a system gain applied to an R-channel image signal among the image signals, and $\Delta Sg$ is a rate of change of a system gain applied to a G-channel image signal among the image signals.

Another aspect of the present invention provides an observation apparatus comprising: a light source unit that generates illumination light by using a plurality of solid-state illumination devices; an image-acquisition device that acquires an image of an object illuminated with the illumination light generated by the light source unit; an image processing unit that processes image signals acquired by the image-acquisition device; and a control unit that controls at least one of the light source unit and the image processing unit. At least one of the solid-state illumination devices of the light source unit has a peak in a G channel, at least another one of the solid-state illumination devices of the light source unit has a peak in a B channel, and, when the control unit increases the amount of the illumination light emitted from the light source unit, the control unit performs control so as to satisfy Conditional Expression (3), and, when the control unit reduces the amount of the illumination light emitted from the light source unit, the control unit performs control so as to satisfy Conditional Expression (4):

$$\Delta Sb/\Delta Sg > 1 \quad (3)$$

$$\Delta Sb/\Delta Sg < 1 \quad (4)$$

where $\Delta Sb$ is a rate of change of a system gain applied to a B-channel image signal among the image signals, and $\Delta Sg$ is a rate of change of a system gain applied to a G-channel image signal among the image signals.

DESCRIPTION OF EMBODIMENTS

An observation apparatus 1 according to an embodiment of the present invention will be described below with reference to the drawings.

Figure 1:
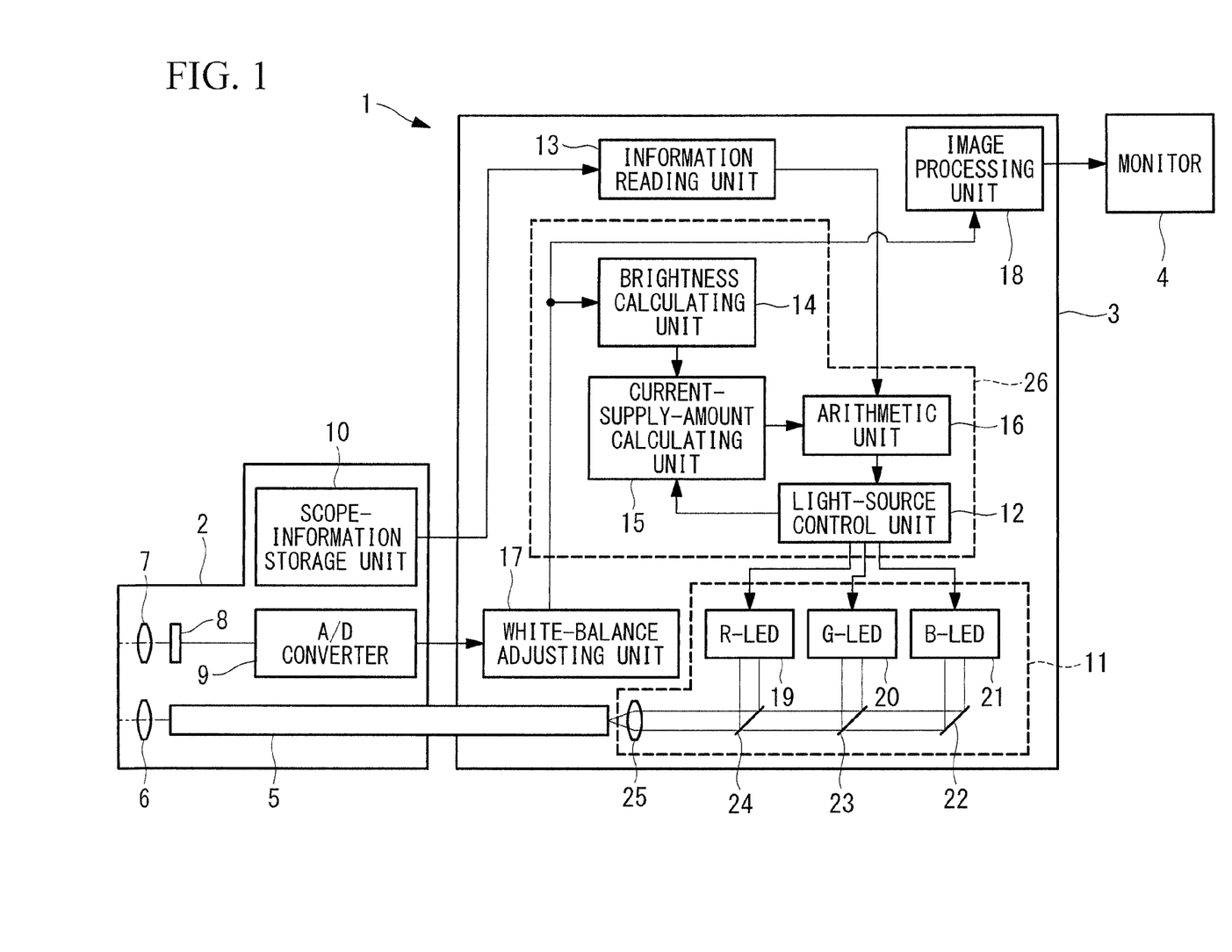
FIG. 1 is a diagram showing the overall configuration of an observation apparatus according to an embodiment of the present invention.

The observation apparatus 1 according to this embodiment is, for example, an endoscope apparatus and includes, as shown in FIG. 1, an elongated insertion part 2 that is to be inserted in the body, an apparatus body 3 that is connected to the proximal end of the insertion part 2, and a monitor 4.

The insertion part 2 includes an optical fiber 5, which is disposed over substantially the entire length in the longitudinal direction and which guides illumination light; an illumination lens 6 that emits the illumination light guided by the optical fiber 5 from the distal end of the insertion part 2; an objective lens 7 that collects reflected light, which is the illumination light reflected by a subject in the body; and an image-acquisition device 8 that acquires an image of the light collected by the objective lens 7. The image-acquisition device 8 is, for example, a CCD or a CMOS imager.

The insertion part 2 is also provided with an A/D converter 9 that performs analog to digital conversion of an image signal acquired by the image-acquisition device 8; and a scope-information storage unit 10 that stores identification information of the insertion part 2.

The apparatus body 3 includes a light source unit 11 that emits illumination light, and a control unit 26 that controls the light source unit 11.

The apparatus body 3 also includes an information reading unit 13 that reads the identification information of the insertion part 2 from the scope-information storage unit 10 of the insertion part 2 when the insertion part 2 is attached to the apparatus body 3; a white-balance adjusting unit 17 that adjusts the white balance of the image signal output from the A/D converter 9 of the insertion part 2; and an image processing unit 18 that generates an observation image by processing the image signal that has been subjected to white-balance adjustment, and outputs the observation image to the monitor 4.

The control unit 26 includes a brightness calculating unit 14 that calculates the average brightness value from the image signal output from the white-balance adjusting unit 17; a light-source control unit 12 that supplies an electric current to the light source unit 11; a current-supply-amount calculating unit 15 that calculates the target current supply amount from the average brightness value calculated by the brightness calculating unit 14 and the information about the amount of current supplied from the light-source control unit 12 to the light source unit 11; and an arithmetic unit 16 that calculates an instruction signal to the light-source control unit 12, on the basis of the target current supply amount output from the current-supply-amount calculating unit 15.

Figure 2:
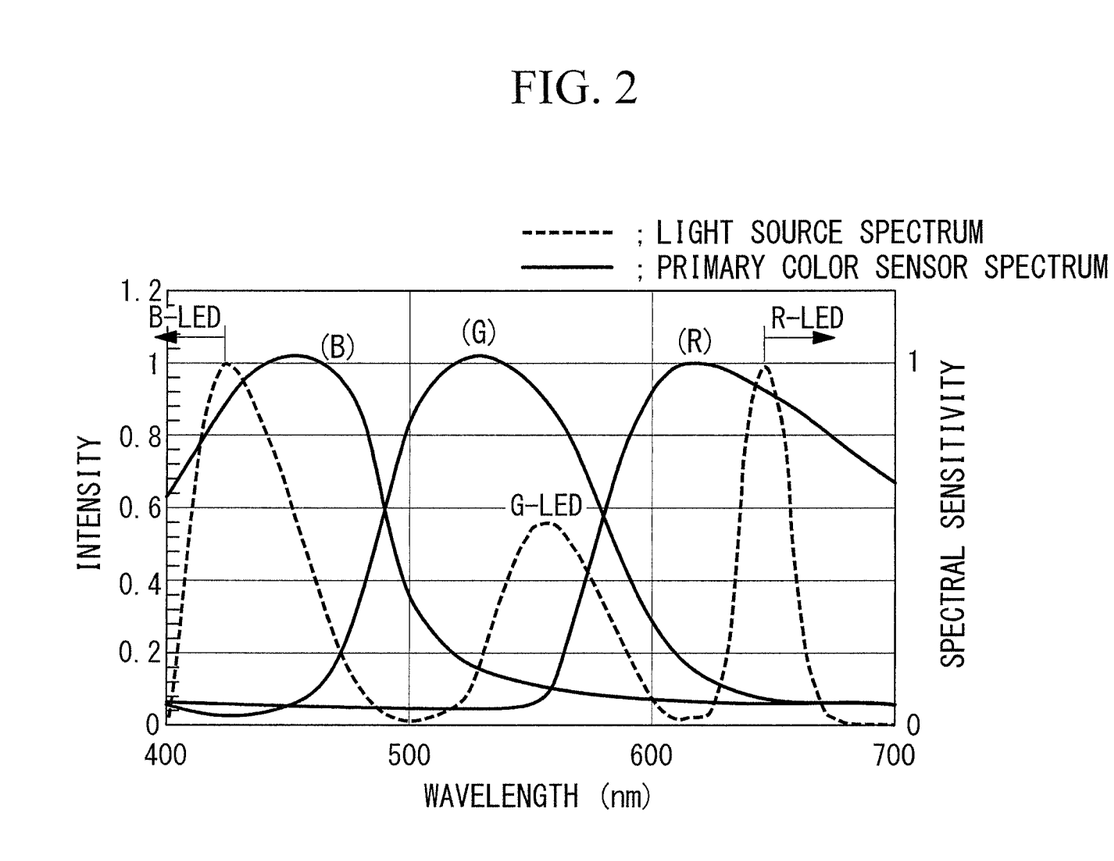
FIG. 2 is a diagram showing an example of wavelength characteristics of solid-state illumination devices and an image-acquisition device of the observation apparatus in FIG. 1.

The light source unit 11 includes an R-LED (solid-state illumination device) 19 that emits light having a peak in an R channel, a G-LED (solid-state illumination device) 20 that emits light having a peak in a G channel, and a B-LED (solid-state illumination device) 21 that emits light having a peak in a B channel, as shown in FIG. 2; a mirror 22 and dichroic mirrors 23 and 24 that multiplex the illumination light emitted from these LEDs (hereinbelow also referred to as simply "solid-state illumination devices") 19 to 21 to compose white illumination light; and a light-focusing lens 25 that focuses and makes the composed white illumination light enter the incident end of the optical fiber 5.

The current-supply-amount calculating unit 15 calculates the difference value between a preset brightness value and the average brightness value calculated from the image signal and input from the brightness calculating unit 14, and calculates the target current supply amount on the basis of the difference value and the amount of current supplied to the G-LED 20. For example, in the case where the amount of current supplied to the G-LED 20 is 100 mA, when a difference value that makes the preset brightness value twice the calculated average brightness value is calculated, a target current supply amount of 200 mA is calculated and output to the arithmetic unit 16.

Figure 3:
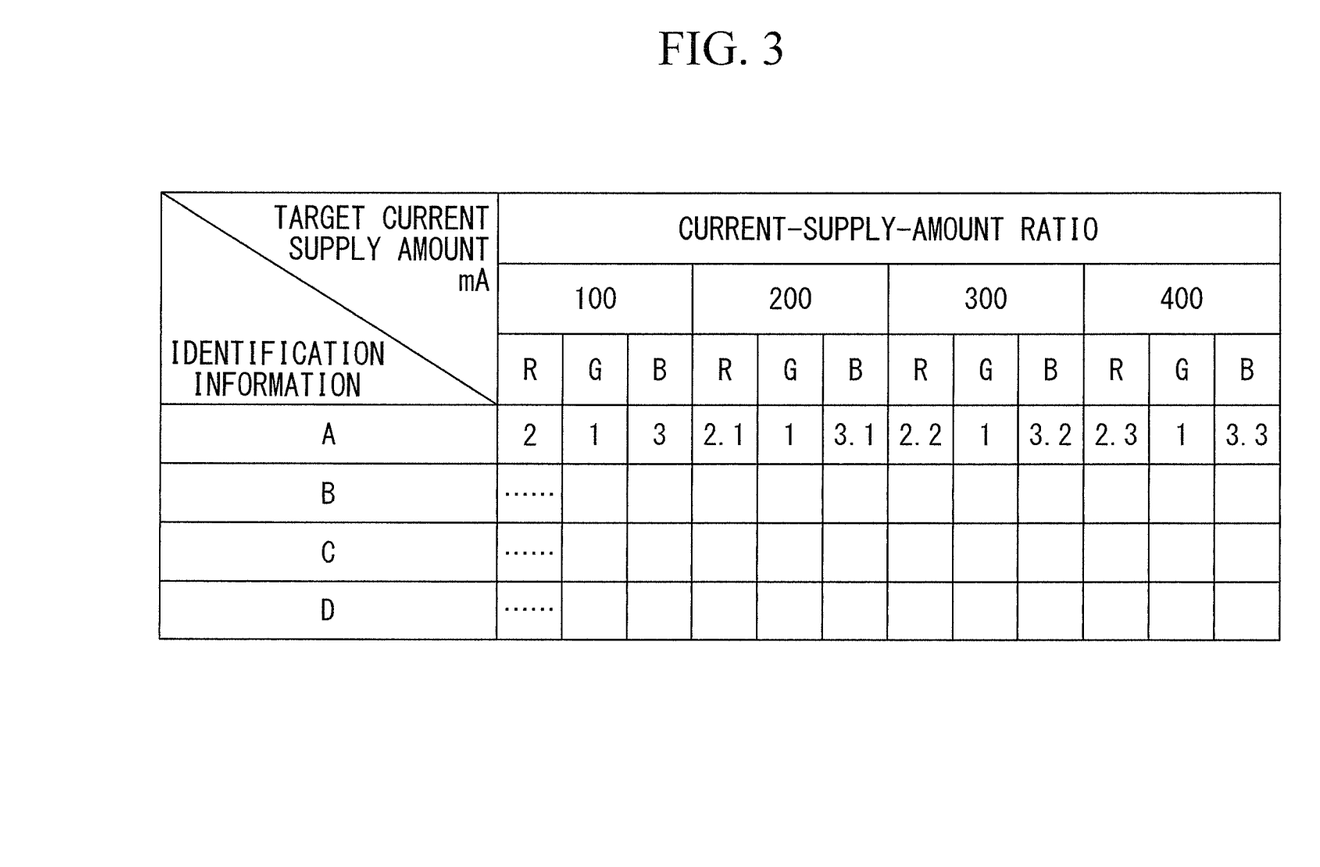
FIG. 3 is a diagram showing an example of a table stored in an arithmetic unit of the observation apparatus in FIG. 1.

The arithmetic unit 16 stores the table shown in FIG. 3. This table shows the correspondence among the identification information of the insertion part 2, the target current supply amount, and the ratio of the amounts of current supplied to the respective solid-state illumination devices 19 to 21.

For example, when the insertion part 2 has identification information A, and when the target current supply amount is 100 mA, the ratio, R:G:B, of the amounts of current to be supplied to the R-LED 19, G-LED 20, and B-LED 21 is set to be 2:1:3 in this table.

In this embodiment, the ratios recorded in this table are set such that, as the target current supply amount increases, the proportions of the amounts of current supplied to the R-LED 19 and the B-LED 21 increase relative to the proportion of the amount of current supplied to the G-LED 20. For example, with respect to the insertion part 2 with the identification information A, when the target current supply amount is 200 mA, the ratio, R:G:B, is set to be 2.1:1:3.1, and when the target current supply amount is 300 mA, the ratio, R:G:B, is set to be 2.2:1:3.2.

More specifically, when the target current supply amount increases, Expression (1) and Expression (3) below are satisfied, and when the target current supply amount decreases, Expression (2) and Expression (4) are satisfied.

$$\Delta Sr/\Delta Sg > 1 \tag{1}$$

$$\Delta Sr/\Delta Sg < 1 \tag{2}$$

$$\Delta Sb/\Delta Sg > 1 \tag{3}$$

$$\Delta Sb/\Delta Sg < 1 \tag{4}$$

where $\Delta Sr$ is a rate of change of a system gain applied to an R-channel image signal, $\Delta Sg$ is a rate of change of a system gain applied to a G-channel image signal, and $\Delta Sb$ is a rate of change of a system gain applied to a B-channel image signal.

In this embodiment, the rate of change of the system gains $\Delta Sr$, $\Delta Sg$, and $\Delta Sb$ may be rates of change of total light amounts $\Delta Lr$, $\Delta Lg$, and $\Delta Lb$ of the R-LED 19, the G-LED 20, and the B-LED 21. In other words, Expressions (1) to (4) above may be replaced by Expression (5) to (8) below.

$$\Delta Lr/\Delta Lg > 1 \tag{5}$$

$$\Delta Lr/\Delta Lg < 1 \tag{6}$$

$$\Delta Lb/\Delta Lg > 1 \tag{7}$$

$$\Delta Lb/\Delta Lg < 1 \tag{8}$$

where $\Delta Lr$ is a rate of change of a total light amount of the R-LED 19, which has a peak in the R channel, $\Delta Lg$ is a rate of change of a total light amount of the G-LED 20, which has a peak in the G channel, and $\Delta Lb$ is a rate of change of a total light amount of the B-LED 21, which has a peak in the B channel.

The arithmetic unit 16 calculates, from the ratio read out of the table and the target current supply amount, the amounts of current to be supplied to the respective solid-state illumination devices 19 to 21, and send the result to the light-source control unit 12.

The light-source control unit 12 supplies current to the respective solid-state illumination devices 19 to 21 according to the amounts of current to be supplied, which are sent from the arithmetic unit 16.

More specifically, in the above-described example, when the target current supply amount is set to 100 mA, on the basis of the corresponding target current supply amount and ratio, 2:1:3, the arithmetic unit 16 supplies 200 mA, 100 mA, and 300 mA to the R-LED 19, the G-LED 20, and the B-LED 21, respectively, and, when the target current supply amount is set to 200 mA, on the basis of the corresponding target current supply amount and ratio, 2.1:1:3.1, the arithmetic unit 16 supplies 420 mA, 200 mA, and 620 mA to the R-LED 19, the G-LED 20, and the B-LED 21, respectively.

Note that, when a value among values stored in the table is calculated as the target current supply amount, a ratio may be interpolated and output, on the basis of the current supply amounts that are stored in the table and that sandwich the calculated target current supply amount therebetween.

The operation of the thus-configured observation apparatus 1 according to this embodiment will be described below.

When observation is to be performed using the observation apparatus 1 according to this embodiment, the insertion part 2 is attached to the apparatus body 3, the insertion part 2 is inserted into the body, and the light-source control unit 12 is actuated, with the distal end of the insertion part 2 facing a portion to be observed.

Once the insertion part 2 is attached to the apparatus body 3, the identification information of the insertion part 2 stored in the scope-information storage unit 10 provided in the insertion part 2 is read by the information reading unit 13 of the apparatus body 3. Herein, a case where the identification information of the insertion part 2 is "A" will be described. The read identification information is sent to the arithmetic unit 16. By using, for example, "100 mA" as an initial target current supply amount, the arithmetic unit 16 reads out a ratio from the table on the basis of the identification information of the insertion part 2 sent from the information reading unit 13 and the target current supply amount, calculates the amounts of current to be supplied to the respective solid-state illumination devices 19 to 21, and instructs them to the light-source control unit 12.

The light-source control unit 12 supplies current to the R-LED 19, the G-LED 20, and the B-LED 21 according to a current-supply-amount instruction signal sent from the arithmetic unit 16. As a result, the R-LED 19 emits light having a peak in the R channel, the G-LED 20 emits light having a peak in the G channel, and the B-LED 21 emits light having a peak in the B channel.

The beams of light emitted from the respective solid-state illumination devices 19 to 21 are multiplexed by the mirror 22 and the dichroic mirrors 23 and 24 into white illumination light, are focused by the light-focusing lens 25, and are made to enter the incident end of the optical fiber 5. The illumination light entering the optical fiber 5 is guided through the optical fiber 5, exits from the exit end of the optical fiber 5 disposed at the distal end of the insertion part 2, and is focused by the illumination lens 6 to irradiate the observation object.

The light reflected by the observation object is collected by the objective lens 7 disposed at the distal end of the insertion part 2, and an image thereof is acquired by the image-acquisition device 8. The image signal acquired by the image-acquisition device 8 is converted from analog to digital by the A/D converter 9 and is then sent to the apparatus body 3, where the white-balance adjusting unit 17 adjusts the white balance, and the image processing unit 18 performs image processing. As a result, an observation image is generated, which is sent to the monitor 4 to be displayed. As a result, the observer can observe the portion to be observed in the body, by using the observation image displayed on the monitor 4.

In this case, the image signal that has been acquired by the image-acquisition device 8 and has been converted from analog to digital is subjected to white-balance adjustment and is then input to the brightness calculating unit 14, where an average brightness value is calculated. Then, the average brightness value is input to the current-supply-amount calculating unit 15. Meanwhile, the light-source control unit 12 inputs the amount of current to be supplied to the G-LED 20 to the current-supply-amount calculating unit 15.

The current-supply-amount calculating unit 15 calculates the difference between the preset brightness value and the average brightness value input from the brightness calculating unit 14, and, on the basis of the difference value and the current amount supplied to the G-LED 20, a new target current supply amount is calculated.

When the preset brightness value and the average brightness value input from the brightness calculating unit 14 are equal, the difference value is zero, and hence, the target current supply amount does not change.

In contrast, when the distance between the portion to be observed, which is to be irradiated with the illumination light, and the distal end surface of the insertion part 2 has changed, the average brightness value of the image signal acquired by the image-acquisition device 8 changes.

For example, when the distance between the portion to be observed and the distal end surface of the insertion part 2 increases, the average brightness value decreases, whereas, when the aforementioned distance decreases, the average brightness value increases. When the distance has increased, the current-supply-amount calculating unit calculates a target current supply amount that is higher than the amount of current currently supplied. In the case where the amount of current currently supplied is 100 mA, when the brightness of the image signal has changed and a target current supply amount of 200 mA is calculated, the arithmetic unit 16, by reading out a current-supply-amount ratio, R:G:B, which is 2.1:1:3.1, corresponding to the identification information A and the target current supply amount of 200 mA in the table, and multiplying this ratio by the target current supply amount, generates an instruction that instructs the supply of 420 mA, 200 mA, and 620 mA to the R-LED 19, the G-LED 20, and the B-LED 21, respectively, and outputs this instruction to the light-source control unit 12.

In this case, the amounts of current to be supplied to the R-LED 19 and the B-LED 21 are increased at higher rates than the amount of current to be supplied to the G-LED 20. More specifically, when the temperatures of the R-LED 19 and the B-LED 21 increase as a result of the amounts of current supplied thereto being increased, the peak wavelengths are shifted in the directions in which the sensitivity of the image-acquisition device 8 decreases, as shown by arrows in FIG. 2. Hence, by supplying more current, the total light amounts of the R-LED 19 and the B-LED 21 is increased.

As a result, the rate of change of the total light amount, $\Delta Lr$, of the R-LED 19 is 2.1/2=1.05, the rate of change of the total light amount, $\Delta Lg$, of the G-LED is 1/1=1, and the rate of change of the total light amount, $\Delta Lb$, of the B-LED is 3.1/3=1.033, and thus, Expressions (5) and (6) are satisfied. With this configuration, it is possible to compensate for a decrease in sensitivity of the image-acquisition device 8 due to shifts of the peak wavelengths, to maintain the color balance, and to obtain an observation image having high color reproducibility.

Conversely, when the distance between the portion to be observed and the distal end surface of the insertion part 2 decreases, the current-supply-amount calculating unit 15 calculates a target current supply amount that is lower than the amount of current currently supplied. In the case where the amount of current currently supplied is 200 mA, when the brightness of the image signal has changed and a target current supply amount of 100 mA is calculated, the arithmetic unit 16 reads out the current-supply-amount ratio, R:G:B, which is 2:1:3, corresponding to the identification information A and a target current supply amount of 100 mA in the table, multiplies this ratio by the target current supply amount to generate an instruction that instructs the supply of 200 mA, 100 mA, and 300 mA to the R-LED 19, the G-LED 20, and the B-LED 21, respectively, and outputs this instruction to the light-source control unit 12.

In this case, the amounts of current to be supplied to the R-LED 19 and the B-LED 21 are reduced at lower rates than the amount of current to be supplied to the G-LED 20. More specifically, when the temperatures of the R-LED 19 and the B-LED 21 decrease as a result of the amounts of current supplied thereto being reduced, the peak wavelengths are shifted in the directions in which the sensitivity of the image-acquisition device 8 increases. Hence, by supplying less current, the amounts of light emitted from the solid-state illumination devices 19 and 21 are reduced.

As a result, the rate of change of the total light amount, ΔLr, of the R-LED 19 is 2/2.1=0.95, the rate of change of the total light amount, ΔLg, of the G-LED 20 is 1/1=1, and the rate of change of the total light amount, ΔLb, of the B-LED 21 is 3/3.1=0.97, and Expressions (7) and (8) are satisfied. With this configuration, it is possible to compensate for an increase in sensitivity of the image-acquisition device 8 due to shifts of the peak wavelengths, to maintain the color balance, and to obtain an observation image having high color reproducibility.

Note that, in this embodiment, although the control unit 26 controls the light source unit 11, and the rate of change of the total light amounts ΔLr, ΔLg, and ΔLb of the R-LED 19, the G-LED 20, and the B-LED 21 have been shown as an example of the system gains Sr, Sg, and Sb, the present invention is not limited thereto.

For example, it is also possible that the white balance is added to the image signals in the white-balance adjusting unit 17, on the basis of the identification information of the insertion part 2 read by the information reading unit 13, and that, instead of adjusting the light amounts of the solid-state illumination devices 19 to 21 to compensate for a decrease in sensitivity of the image-acquisition device 8 due to increases in the amounts of current supplied, the gains used as multipliers in the image processing unit 18 and the white-balance adjusting unit 17 are adjusted.

Figure 4:
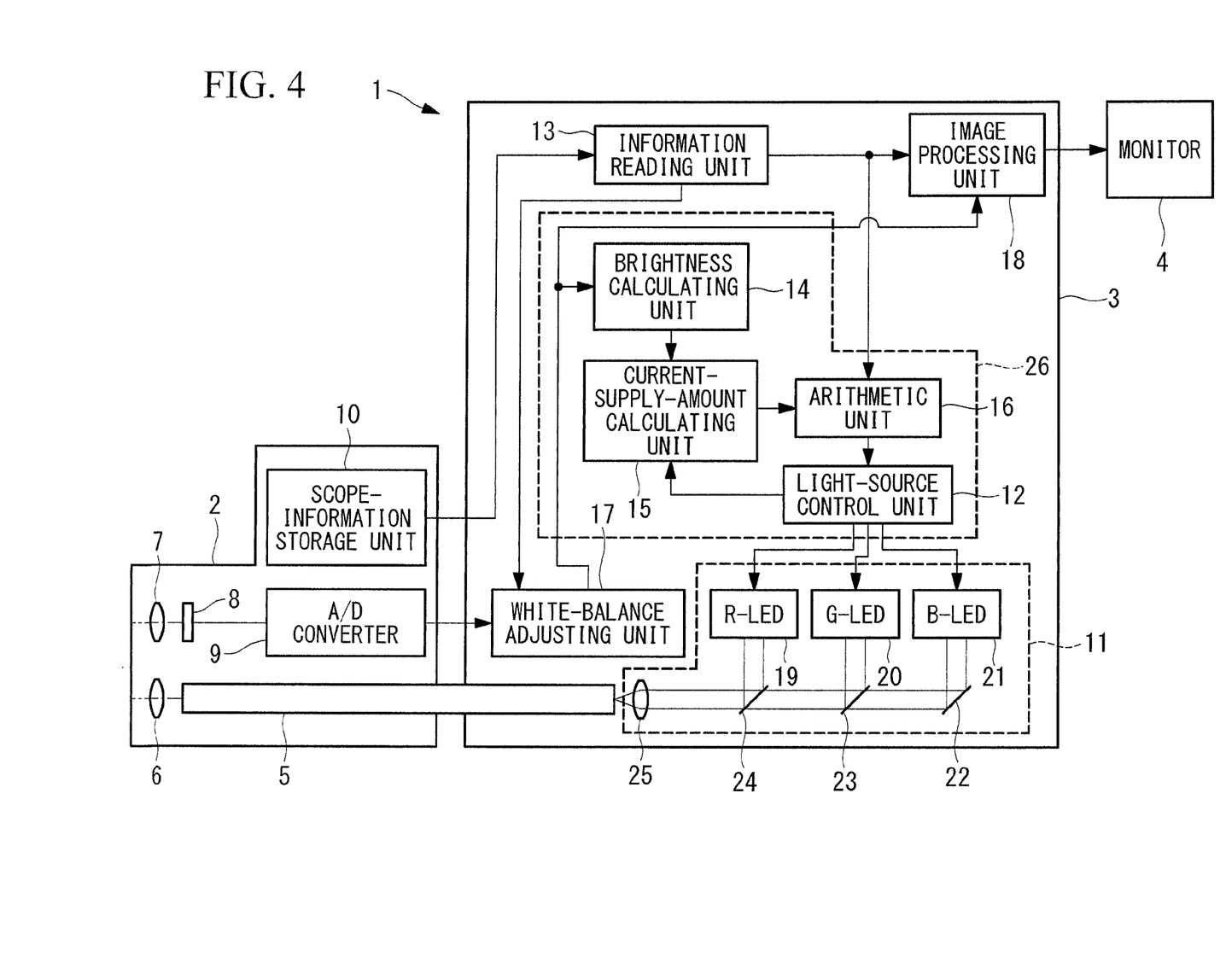
FIG. 4 is a diagram showing the overall configuration of a modification of the observation apparatus in FIG. 1.
Figure 5:
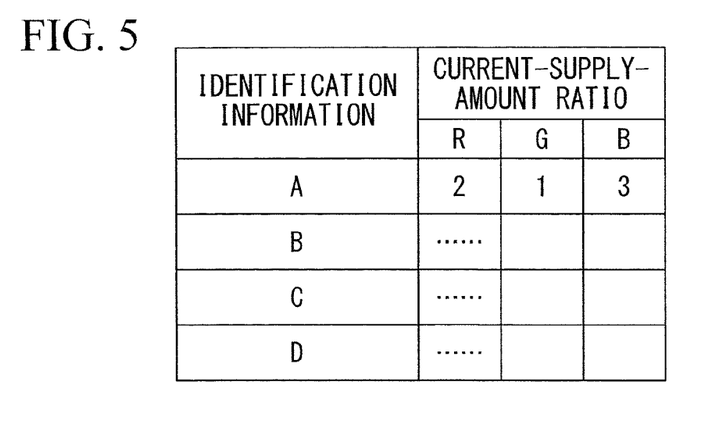
FIG. 5 is a diagram showing an example of a table stored in an arithmetic unit of an observation apparatus in FIG. 4.

More specifically, as shown in FIG. 4, the target current supply amount calculated by the current-supply-amount calculating unit 15 and the identification information of the insertion part 2 read from the information reading unit 13 are input to the arithmetic unit 16, and the arithmetic unit 16 calculates the amounts of current to be supplied to the respective solid-state illumination devices 19 to 21 by multiplying the current-supply-amount ratio read out from the table shown in FIG. 5 and the target current supply amount. By using a constant current-supply-amount ratio regardless of the target current supply amount, even when the amounts of light emitted from the respective solid-state illumination devices 19 to 21 change due to light modulation, the rate of change of the total light amounts ΔLr, ΔLg, and ΔLb of the R-LED 19, the G-LED 20, and the B-LED 21 are set equal.

Figure 6:
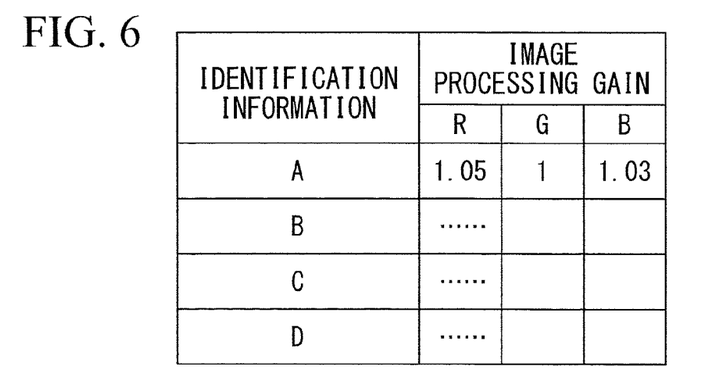
FIG. 6 is a diagram showing an example of a table stored in an image processing unit of the observation apparatus in FIG. 4.
Figure 7:
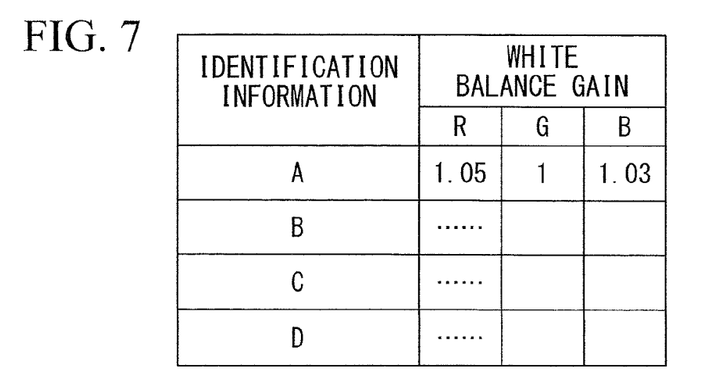
FIG. 7 is a diagram showing an example of a table stored in a white-balance adjusting unit of the observation apparatus in FIG. 4.

The image processing unit 18 and the white-balance adjusting unit 17 store the tables shown in FIGS. 6 and 7, and, on the basis of the identification information of the insertion part 2 input from the information reading unit 13, image processing gains and white balance gains are read out. The image processing gains may be, for example, coefficients of a color-conversion matrix.

Regarding these gains, similarly to the table in FIG. 3, the image-processing gain ratio and the white-balance gain ratio are determined according to the identification information.

Figure 8:
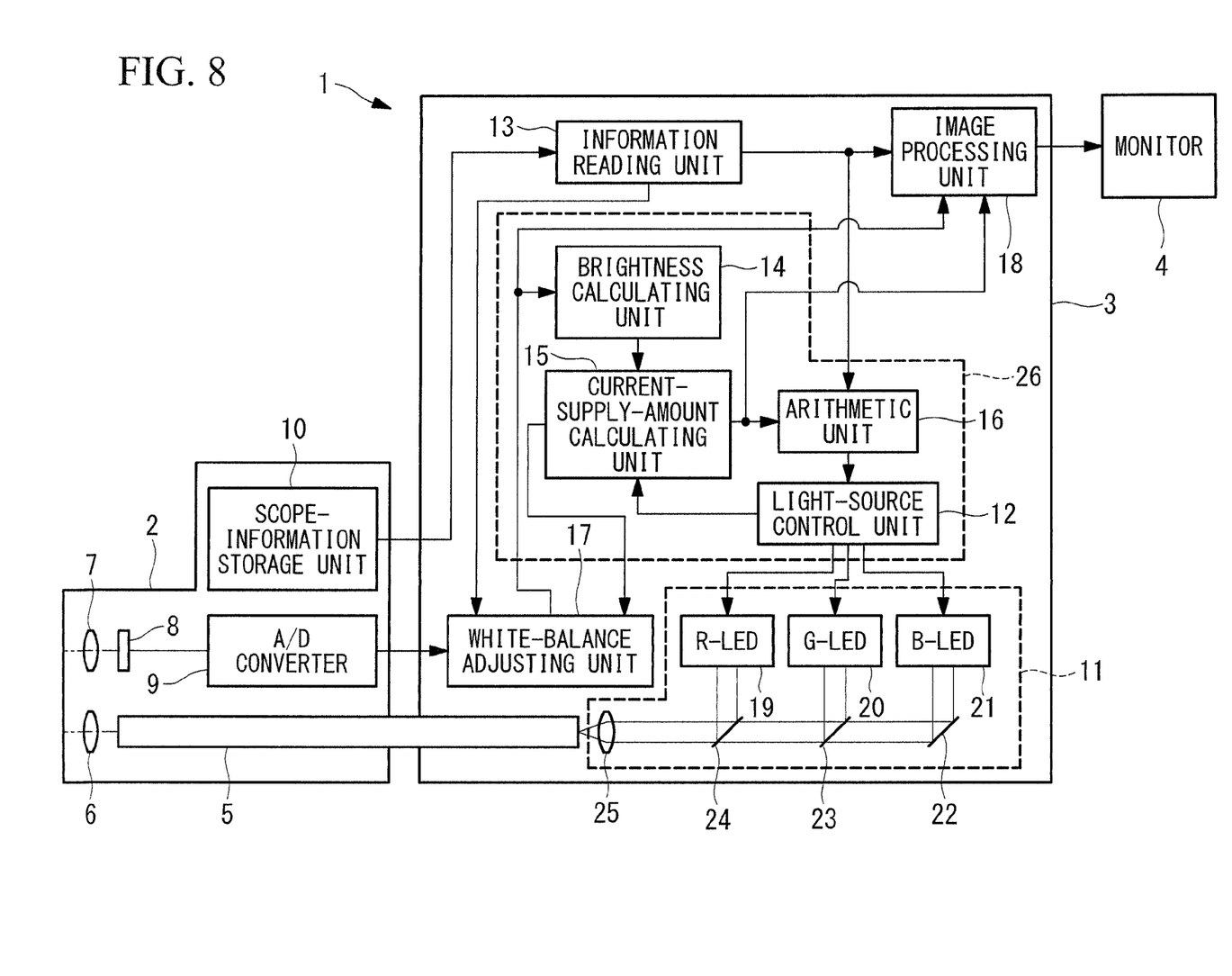
FIG. 8 is a diagram showing the overall configuration of another modification of the observation apparatus in FIG. 1.
Figure 9:
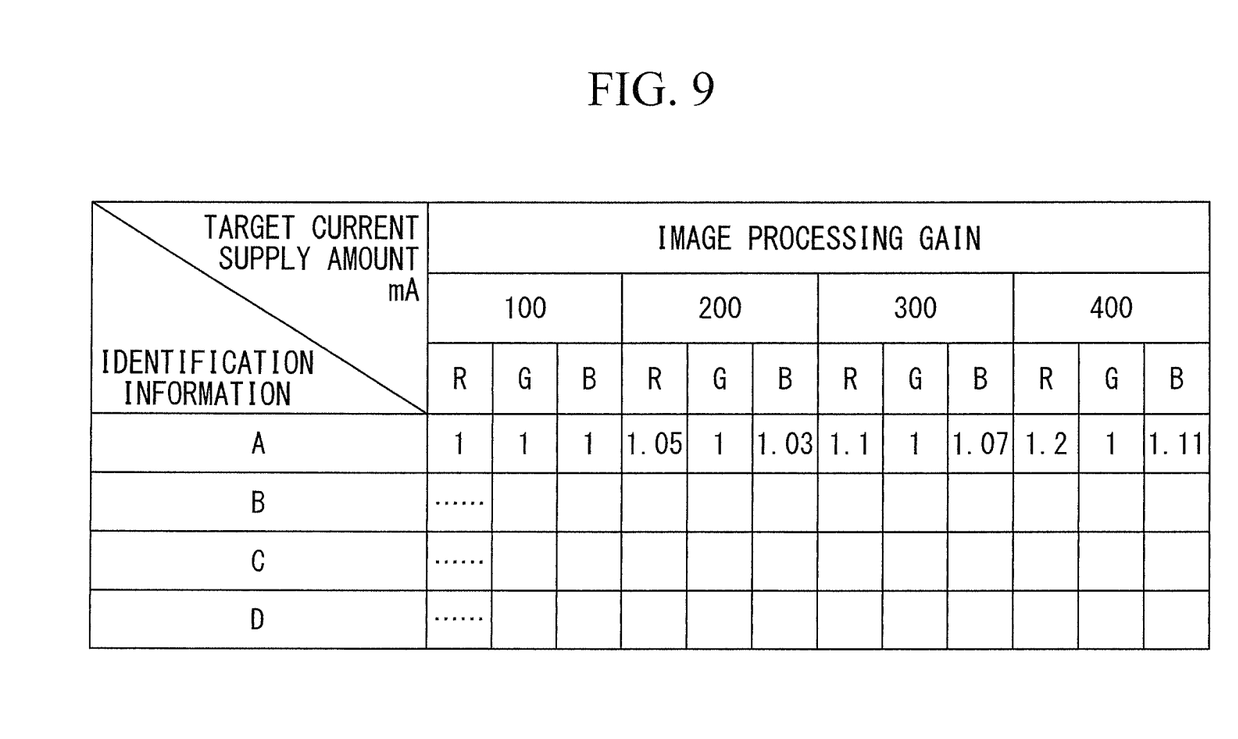
FIG. 9 is a diagram showing an example of a table stored in an image processing unit of an observation apparatus in FIG. 8.
Figure 10:
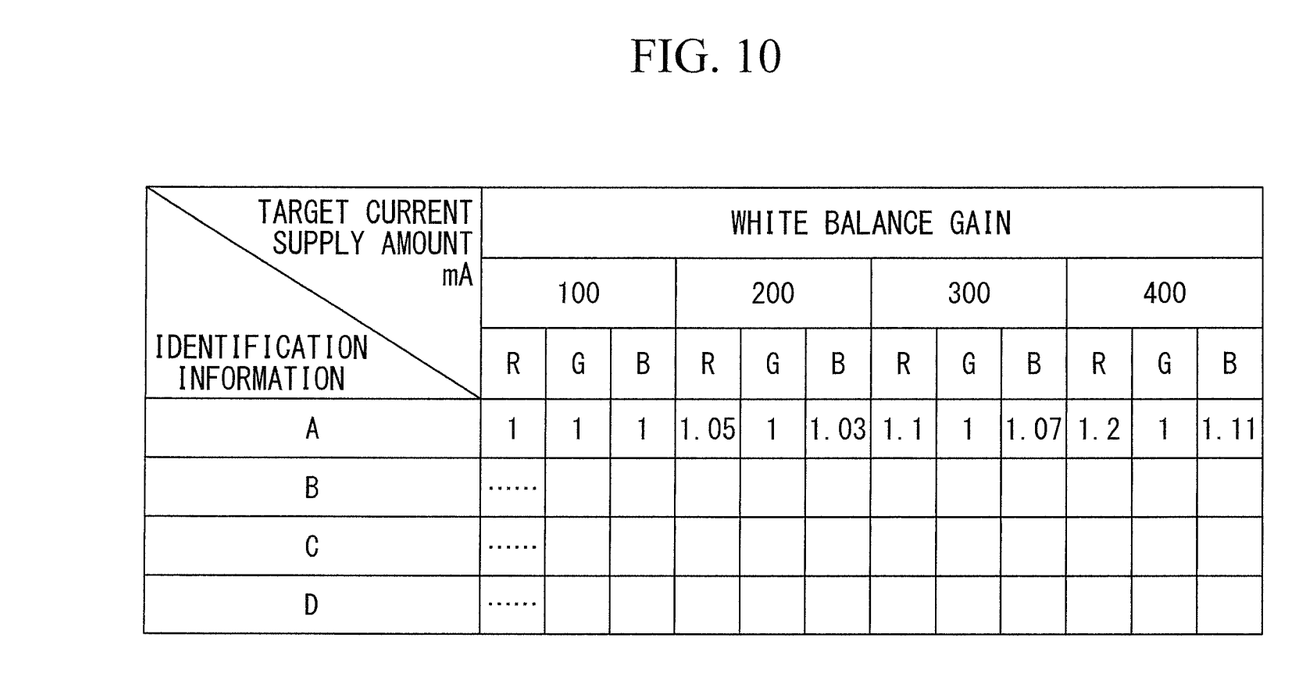
FIG. 10 is a diagram showing an example of a table stored in a white-balance adjusting unit of the observation apparatus in FIG. 8.

Furthermore, it is also possible that the image processing unit 18 and the white-balance adjusting unit 17 store the tables shown in FIGS. 9 and 10, and, as shown in FIG. 8, the image processing gains and the white balance gains are read out on the basis of the identification information of the insertion part 2 input from the information reading unit 13 and the target current supply amount calculated by the current-supply-amount calculating unit 15.

Regarding these gains, similarly to the table in FIG. 3, the image-processing gain ratio and the white-balance gain ratio are determined according to the target current supply amount and the identification information, and, as the target current supply amount increases, the proportions of the gains by which the R signal and the B signal are multiplied increase relative to the gain by which the G signal is multiplied.

More specifically, gains Gr, Gg, and Gb, such as image processing gains Gr1, Gg1, or Gb1 or white balance gains Gr2, Gg2, and Gb2, which are used in image processing, may be employed as the system gains Sr, Sg, and Sb. Herein, Gg is a gain by which the G signal in the image signal is multiplied, Gr is a gain by which the R signal in the image signal is multiplied, and Gb is a gain by which the B signal in the image signal is multiplied, and, for example, Gr=Gr1× Gr2, Gg=Gg1×Gg2, and Gb=Gb1×Gb2.

When the target current supply amount increases, Expression (9) and Expression (11) below are satisfied, and when the target current supply amount decreases, Expression (10) and Expression (12) are satisfied.

$$Gr/Gg > 1 \tag{9}$$

$$Gr/Gg < 1 \tag{10}$$

$$Gb/Gg > 1 \tag{11}$$

$$Gb/Gg < 1 \tag{12}$$

Also in these configurations, when the distance between the portion to be observed and the distal end surface of the insertion part 2 increases, and the target current supply amount increases, the amounts of current to be supplied to the respective solid-state illumination devices 19 and 21 increase. As a result, the peak wavelengths of the R-LED 19 and the B-LED 21 are shifted, decreasing the sensitivity of the image-acquisition device 8, and thus, an image signal in which the R signal and the B signal are lower than the G signal is acquired. Thus, in the white-balance adjusting unit 17 and the image processing unit 18, by multiplying the image signals by the gains Gr, Gg, and Gb used to amplify the R signal and the B signal by greater degrees relative to the G signal according to the ratio stored in the table, it is possible to is compensate for an increase in the sensitivity of the image-acquisition device 8 due to shifts of the peak wavelengths, to maintain the color balance, and to obtain an observation image having high color reproducibility.

Although example cases where one of the ratio of the total light amounts and the gains by which the image signals are multiplied in the image processing is employed according to the target current supply amount has been shown, instead, both of them may be employed.

Furthermore, although an example observation apparatus having the light source unit 11 that includes all of the R-LED 19, the G-LED 20, and the B-LED 21 and that multiplexes the beams into white illumination light and emits the while light has been shown, the present invention may also be applied to a case where illumination is performed with a light source unit 11 that has only the R-LED 19 and the G-LED 20, or only the G-LED 20 and the B-LED 21.

From the above-described embodiment and modifications thereof, the following aspects of the invention are derived.

According to an aspect of the present invention, there is provided an observation apparatus including: a light source unit that generates illumination light by using a plurality of solid-state illumination devices; an image-acquisition device that acquires an image of an object illuminated with the illumination light generated by the light source unit; an image processing unit that processes image signals acquired by the image-acquisition device; and a control unit that controls at least one of the light source unit and the image processing unit. At least one of the solid-state illumination devices of the light source unit has a peak in a G channel, at least another one of the solid-state illumination devices of the light source unit has a peak in an R channel, and, when the control unit increases the amount of the illumination light emitted from the light source unit, the control unit performs control so as to satisfy Conditional Expression (1), and, when the control unit reduces the amount of the illumination light emitted from the light source unit, the control unit performs control so as to satisfy Conditional Expression (2):

$$\Delta Sr/\Delta Sg > 1 \quad (1)$$

$$\Delta Sr/\Delta Sg < 1 \quad (2)$$

where $\Delta Sr$ is a rate of change of a system gain applied to an R-channel image signal among the image signals, and $\Delta Sg$ is a rate of change of a system gain applied to a G-channel image signal among the image signals.

According to this aspect, an observable image is generated by irradiating the object with the illumination light emitted from the light source unit, by acquiring, with the image-acquisition device, an image of light reflected by the object, and by processing, with the image processing unit, the acquired image signals. When the brightness of the generated image has changed, and the light is to be modulated, the control unit controls at least one of the light source unit and the image processing unit to adjust the brightness of the image.

In this case, when the amount of the illumination light emitted from the light source unit is increased, the amounts of current supplied to the respective solid-state illumination devices increase, and, due to an increase in temperature of a solid-state illumination device that has a peak in the R channel, the peak wavelength is shifted to the long-wavelength side. On the other hand, in the R region, the image-acquisition device becomes less sensitive as the wavelength becomes longer. To counter this situation, the control unit performs control so as to satisfy Conditional Expression (1). As a result, the R-channel image signal is amplified by a greater degree than the G-channel image signal, making it possible to compensate for a decrease in sensitivity of the image-acquisition device due to the shift of the peak wavelength and to obtain an observation image having high color reproducibility.

On the other hand, when the amount of the illumination light emitted from the light source unit is reduced, the amounts of current supplied to the respective solid-state illumination devices decrease, and, due to a decrease in temperature of the solid-state illumination device that has a peak in the R channel, the peak wavelength is shifted to the short-wavelength side. On the other hand, in the R region, the image-acquisition device becomes more sensitive as the wavelength becomes shorter. To counter this situation, the control unit performs control so as to satisfy Conditional Expression (2). As a result, the R-channel image signal is amplified by a smaller degree than the G-channel image signal, making it possible to compensate for an increase in the sensitivity of the image-acquisition device due to the shift of the peak wavelength and to obtain an observation image having high color reproducibility.

Another aspect of the present invention provides an observation apparatus comprising: a light source unit that generates illumination light by using a plurality of solid-state illumination devices; an image-acquisition device that acquires an image of an object illuminated with the illumination light generated by the light source unit; an image processing unit that processes image signals acquired by the image-acquisition device; and a control unit that controls at least one of the light source unit and the image processing unit. At least one of the solid-state illumination devices of the light source unit has a peak in a G channel, at least another one of the solid-state illumination devices of the light source unit has a peak in a B channel, and, when the control unit increases the amount of the illumination light emitted from the light source unit, the control unit performs control so as to satisfy Conditional Expression (3), and, when the control unit reduces the amount of the illumination light emitted from the light source unit, the control unit performs control so as to satisfy Conditional Expression (4):

$$\Delta Sb/\Delta Sg > 1 \quad (3)$$

$$\Delta Sb/\Delta Sg < 1 \quad (4)$$

where $\Delta Sb$ is a rate of change of a system gain applied to a B-channel image signal among the image signals, and $\Delta Sg$ is a rate of change of a system gain applied to a G-channel image signal among the image signals.

According to this aspect, when the amount of the illumination light emitted from the light source unit is increased, the amounts of current supplied to the respective solid-state illumination devices increase, and, due to an increase in temperature of a solid-state illumination device that has a peak in the B channel, the peak wavelength is shifted to the short-wavelength side. On the other hand, in the B region, the image-acquisition device becomes less sensitive as the wavelength becomes shorter. To counter this situation, the control unit performs control so as to satisfy Conditional Expression (3). As a result, the B-channel image signal is amplified by a greater degree than the G-channel image signal, making it possible to compensate for a decrease in sensitivity of the image-acquisition device due to the shift of the peak wavelength and to obtain an observation image having high color reproducibility.

On the other hand, when the amount of the illumination light emitted from the light source unit is reduced, the amounts of current supplied to the respective solid-state illumination devices decrease, and, due to a decrease in temperature of the solid-state illumination device that has a peak in the B channel, the peak wavelength is shifted to the long-wavelength side. On the other hand, in the B region, the image-acquisition device becomes more sensitive as the wavelength becomes longer. To counter this situation, the control unit performs control so as to satisfy Conditional Expression (4). As a result, the B-channel image signal is amplified by a smaller degree than the G-channel image signal, making it possible to compensate for an increase in the sensitivity of the image-acquisition device due to the shift of the peak wavelength and to obtain an observation image having high color reproducibility.

In the above aspect, at least one of the solid-state illumination devices of the light source unit may have a peak in a B channel, and, when the control unit increases the amount of the illumination light emitted from the light source unit, the control unit may perform control so as to satisfy Conditional Expression (1) and Conditional Expression (3), and, when the control unit reduces the amount of the illumination light emitted from the light source unit, the control unit may perform control so as to satisfy Conditional Expression (2) and Conditional Expression (4):

$$\Delta Sb/\Delta Sg > 1 \tag{3}$$

$$\Delta Sb/\Delta Sg < 1 \tag{4}$$

where $\Delta Sb$ is a rate of change of a system gain applied to a B-channel image signal among the image signals, and $\Delta Sg$ is a rate of change of a system gain applied to the G-channel image signal among the image signals.

With this configuration, when the amount of the illumination light emitted from the light source unit is increased, the amounts of current supplied to the respective solid-state illumination devices increase, and, due to increases in temperature, the peak wavelength of the R-channel solid-state illumination device is shifted to the long-wavelength side, and the peak wavelength of the B-channel solid-state illumination device is shifted to the short-wavelength side. On the other hand, in the R region, the image-acquisition device becomes less sensitive as the wavelength becomes longer, and in the B region, the image-acquisition device becomes less sensitive as the wavelength becomes shorter. To counter this situation, the control unit performs control so as to satisfy Conditional Expression (1) and Conditional Expression (3). As a result, the R-channel and B-channel image signals are amplified by greater degrees than the G-channel image signal, making it possible to compensate for a decrease in sensitivity of the image-acquisition device due to shifts of the peak wavelengths and to obtain an observation image having high color reproducibility.

On the other hand, when the amount of the illumination light emitted from the light source unit is reduced, the amounts of current supplied to the respective solid-state illumination devices decrease, and, due to decreases in temperature, the peak wavelength of the R-channel solid-state illumination device is shifted to the short-wavelength side, and the peak wavelength of the B-channel solid-state illumination device is shifted to the long-wavelength side. On the other hand, in the R region, the image-acquisition device becomes less sensitive as the wavelength becomes longer, and, in the B region, the image-acquisition device becomes less sensitive as the wavelength becomes shorter. To counter this situation, the control unit performs control so as to satisfy Conditional Expression (2) and Conditional Expression (4). As a result, the R-channel and B-channel image signals are amplified by smaller degrees than the G-channel image signal, making it possible to compensate for an increase in the sensitivity of the image-acquisition device due to shifts of the peak wavelengths and to obtain an observation image having high color reproducibility.

Furthermore, in the above aspect, when the control unit increases the amount of the illumination light emitted from the light source unit, the control unit may control the solid-state illumination device so as to satisfy Conditional Expression (5), and, when the control unit reduces the amount of the illumination light emitted from the light source unit, the control unit may control the solid-state illumination device so as to satisfy Conditional Expression (6):

$$\Delta Lr/\Delta Lg > 1 \tag{5}$$

$$\Delta Lr/\Delta Lg < 1 \tag{6}$$

where $\Delta Lg$ is a rate of change of a total light amount of a solid-state illumination device that has a peak in the G channel, and $\Delta Lr$ is a rate of change of a total light amount of a solid-state illumination device that has a peak in the R channel.

With this configuration, by controlling the solid-state illumination devices such that the rate of change of the total light amounts satisfy Conditional Expression (5) or Conditional Expression (6), Conditional Expression (1) or Conditional Expression (2) is satisfied, whereby it is possible to obtain an observation image having high color reproducibility.

Furthermore, in the above aspect, when the control unit increases the amount of the illumination light emitted from the light source unit, the control unit may control the solid-state illumination device so as to satisfy Conditional Expression (7), and, when the control unit reduces the amount of the illumination light emitted from the light source unit, the control unit may control the solid-state illumination device so as to satisfy Conditional Expression (8):

$$\Delta Lb/\Delta Lg > 1 \tag{7}$$

$$\Delta Lb/\Delta Lg < 1 \tag{8}$$

where $\Delta Lg$ is a rate of change of a total light amount of a solid-state illumination device that has a peak in the G channel, and $\Delta Lb$ is a rate of change of a total light amount of a solid-state illumination device that has a peak in the B channel.

With this configuration, by controlling the solid-state illumination devices such that the rate of change of the total light amounts satisfy Conditional Expression (7) or Conditional Expression (8), Conditional Expression (3) or Conditional Expression (4) is satisfied, whereby it is possible to obtain an observation image having high color reproducibility.

Furthermore, in the above aspect, when the control unit increases the amount of the illumination light emitted from the light source unit, the control unit may control the solid-state illumination device so as to satisfy Conditional Expression (5) and Conditional Expression (7), and, when the control unit reduces the amount of the illumination light emitted from the light source unit, the control unit may control the solid-state illumination device so as to satisfy Conditional Expression (6) and Conditional Expression (8):

$$\Delta Lr/\Delta Lg > 1 \tag{5}$$

$$\Delta Lr/\Delta Lg < 1 \tag{6}$$

$$\Delta Lb/\Delta Lg > 1 \tag{7}$$

$$\Delta Lb/\Delta Lg < 1 \tag{8}$$

where $\Delta Lg$ is a rate of change of a total light amount of a solid-state illumination device that has a peak in the G channel, $\Delta Lr$ is a rate of change of a total light amount of a solid-state illumination device that has a peak in the R channel, and $\Delta Lb$ is a rate of change of a total light amount of the solid-state illumination device that has a peak in the B channel.

With this configuration, by controlling the solid-state illumination devices such that the rate of change of the total light amounts satisfy Conditional Expression (5) to Conditional Expression (8), Conditional Expression (1) to Conditional Expression (4) are satisfied, whereby it is possible to obtain an observation image having high color reproducibility.

Furthermore, in the above aspect, when the control unit increases the amount of the illumination light emitted from the light source unit, the control unit may control the image processing unit so as to satisfy Conditional Expression (9), and, when the control unit reduces the amount of the illumination light emitted from the light source unit, the control unit may control the image processing unit so as to satisfy Conditional Expression (10):

$$Gr/Gg > 1 \quad (9)$$

$$Gr/Gg < 1 \quad (10)$$

where Gg is a gain by which a G signal in the image signal is multiplied, and Gr is a gain by which an R signal in the image signal is multiplied.

With this configuration, as a result of the control unit controlling the image processing unit to multiply the image signals by gains so as to satisfy Conditional Expression (9) or Conditional Expression (10), Conditional Expression (1) or Conditional Expression (2) is satisfied, whereby it is possible to obtain an observation image having high color reproducibility.

Furthermore, in the above aspect, when the control unit increases the amount of the illumination light emitted from the light source unit, the control unit may control the image processing unit so as to satisfy Conditional Expression (11), and, when the control unit reduces the amount of the illumination light emitted from the light source unit, the control unit may control the image processing unit so as to satisfy Conditional Expression (12):

$$Gb/Gg > 1 \quad (11)$$

$$Gb/Gg < 1 \quad (12)$$

where Gg is a gain by which a G signal in the image signal is multiplied, Gb is a gain by which the B signal in the image signal is multiplied.

With this configuration, as a result of the control unit controlling the image processing unit to multiply the image signals by gains so as to satisfy Conditional Expression (11) or Conditional Expression (12), Conditional Expression (3) or Conditional Expression (4) is satisfied, whereby it is possible to obtain an observation image having high color reproducibility.

Furthermore, in the above aspect, when the control unit increases the amount of the illumination light emitted from the light source unit, the control unit may control the image processing unit so as to satisfy Conditional Expression (9) and Conditional Expression (11), and, when the control unit reduces the amount of the illumination light emitted from the light source unit, the control unit may control the image processing unit so as to satisfy Conditional Expression (10) and Conditional Expression (12):

$$Gr/Gg > 1 \quad (9)$$

$$Gr/Gg < 1 \quad (10)$$

$$Gb/Gg > 1 \quad (11)$$

$$Gb/Gg < 1 \quad (12)$$

where Gg is a gain by which a G signal in the image signal is multiplied, Gr is a gain by which an R signal in the image signal is multiplied, and Gb is a gain by which the B signal in the image signal is multiplied.

With this configuration, as a result of the control unit controlling the image processing unit to multiply the image signals by gains so as to satisfy Conditional Expression (9) to Conditional Expression (12), Conditional Expression (1) to Conditional Expression (4) are satisfied, whereby it is possible to obtain an observation image having high color reproducibility.

REFERENCE SIGNS LIST

1 observation apparatus
8 image-acquisition device
11 light source unit
18 image processing unit
19 R-LED (solid-state illumination device)
20 G-LED (solid-state illumination device)
21 B-LED (solid-state illumination device)
26 control unit

The invention claimed is:

1. An observation apparatus comprising:
a light source unit that generates illumination light by using a plurality of solid-state illumination devices;
an image-acquisition device that acquires an image of an object illuminated with the illumination light generated by the light source unit;
an image processing unit that processes image signals acquired by the image-acquisition device; and
a control unit that controls at least one of the light source unit and the image processing unit, wherein
at least one of the solid-state illumination devices of the light source unit has a peak in a G channel,
at least another one of the solid-state illumination devices of the light source unit has a peak in an R channel, and, when the control unit increases an amount of the illumination light emitted from the light source unit, the control unit performs control so as to satisfy Conditional Expression (1), and, when the control unit reduces the amount of the illumination light emitted from the light source unit, the control unit performs control so as to satisfy Conditional Expression (2):

$$\Delta Sr/\Delta Sg > 1 \quad (1)$$

$$\Delta Sr/\Delta Sg < 1 \quad (2)$$

where $\Delta Sr$ is a rate of change of a system gain applied to an R-channel image signal among the image signals, and $\Delta Sg$ is a rate of change of a system gain applied to a G-channel image signal among the image signals.

2. An observation apparatus comprising:
a light source unit that generates illumination light by using a plurality of solid-state illumination devices;
an image-acquisition device that acquires an image of an object illuminated with the illumination light generated by the light source unit;
an image processing unit that processes image signals acquired by the image-acquisition device; and
a control unit that controls at least one of the light source unit and the image processing unit, wherein
at least one of the solid-state illumination devices of the light source unit has a peak in a G channel,
at least another one of the solid-state illumination devices of the light source unit has a peak in a B channel, and, when the control unit increases the amount of the illumination light emitted from the light source unit, the control unit performs control so as to satisfy Conditional Expression (3), and, when the control unit reduces the amount of the illumination light emitted from the light source unit, the control unit performs control so as to satisfy Conditional Expression (4):

$$\Delta Sb/\Delta Sg > 1 \quad (3)$$

$$\Delta Sb/\Delta Sg < 1 \quad (4)$$

where $\Delta Sb$ is a rate of change of a system gain applied to a B-channel image signal among the image signals, and $\Delta Sg$ is a rate of change of a system gain applied to a G-channel image signal among the image signals.

3. The observation apparatus according to claim 1, wherein
at least one of the solid-state illumination devices of the light source unit has a peak in a B channel, and,
when the control unit increases the amount of the illumination light emitted from the light source unit, the control unit performs control so as to satisfy Conditional Expression (1) and Conditional Expression (3), and, when the control unit reduces the amount of the illumination light emitted from the light source unit, the control unit performs control so as to satisfy Conditional Expression (2) and Conditional Expression (4):

$$\Delta Sb/\Delta Sg > 1 \quad (3)$$

$$\Delta Sb/\Delta Sg < 1 \quad (4)$$

where $\Delta Sb$ is a rate of change of a system gain applied to a B-channel image signal among the image signals, and $\Delta Sg$ is the rate of change of the system gain applied to the G-channel image signal among the image signals.

4. The observation apparatus according to claim 1, wherein, when the control unit increases the amount of the illumination light emitted from the light source unit, the control unit controls the solid-state illumination device so as to satisfy Conditional Expression (5), and, when the control unit reduces the amount of the illumination light emitted from the light source unit, the control unit controls the solid-state illumination device so as to satisfy Conditional Expression (6):

$$\Delta Lr/\Delta Lg > 1 \quad (5)$$

$$\Delta Lr/\Delta Lg < 1 \quad (6)$$

where $\Delta Lg$ is a rate of change of a total light amount of a solid-state illumination device that has a peak in the G channel, and $\Delta Lr$ is a rate of change of a total light amount of a solid-state illumination device that has a peak in the R channel.

5. The observation apparatus according to claim 2, wherein, when the control unit increases the amount of the illumination light emitted from the light source unit, the control unit controls the solid-state illumination device so as to satisfy Conditional Expression (7), and, when the control unit reduces the amount of the illumination light emitted from the light source unit, the control unit controls the solid-state illumination device so as to satisfy Conditional Expression (8):

$$\Delta Lb/\Delta Lg > 1 \quad (7)$$

$$\Delta Lb/\Delta Lg < 1 \quad (8)$$

where $\Delta Lg$ is a rate of change of a total light amount of a solid-state illumination device that has a peak in the G channel, and $\Delta Lb$ is a rate of change of a total light amount of a solid-state illumination device that has a peak in the B channel.

6. The observation apparatus according to claim 3, wherein, when the control unit increases the amount of the illumination light emitted from the light source unit, the control unit controls the solid-state illumination device so as to satisfy Conditional Expression (5) and Conditional Expression (7), and, when the control unit reduces the amount of the illumination light emitted from the light source unit, the control unit controls the solid-state illumination device so as to satisfy Conditional Expression (6) and Conditional Expression (8):

$$\Delta Lr/\Delta Lg > 1 \quad (5)$$

$$\Delta Lr/\Delta Lg < 1 \quad (6)$$

$$\Delta Lb/\Delta Lg > 1 \quad (7)$$

$$\Delta Lb/\Delta Lg < 1 \quad (8)$$

where $\Delta Lg$ is a rate of change of a total light amount of a solid-state illumination device that has a peak in the G channel, $\Delta Lr$ is a rate of change of a total light amount of a solid-state illumination device that has a peak in the R channel, and $\Delta Lb$ is a rate of change of a total light amount of the solid-state illumination device that has a peak in the B channel.

7. The observation apparatus according to claim 1, wherein, when the control unit increases the amount of the illumination light emitted from the light source unit, the control unit controls the image processing unit so as to satisfy Conditional Expression (9), and, when the control unit reduces the amount of the illumination light emitted from the light source unit, the control unit controls the image processing unit so as to satisfy Conditional Expression (10):

$$Gr/Gg > 1 \quad (9)$$

$$Gr/Gg < 1 \quad (10)$$

where $Gg$ is a gain by which a G signal in the image signal is multiplied, and $Gr$ is a gain by which an R signal in the image signal is multiplied.

8. The observation apparatus according to claim 2, wherein, when the control unit increases the amount of the illumination light emitted from the light source unit, the control unit controls the image processing unit so as to satisfy Conditional Expression (11), and, when the control unit reduces the amount of the illumination light emitted from the light source unit, the control unit controls the image processing unit so as to satisfy Conditional Expression (12):

$$Gb/Gg > 1 \quad (11)$$

$$Gb/Gg < 1 \quad (12)$$

where $Gg$ is a gain by which a G signal in the image signal is multiplied, $Gb$ is a gain by which the B signal in the image signal is multiplied.

9. The observation apparatus according to claim 3, wherein, when the control unit increases the amount of the illumination light emitted from the light source unit, the control unit controls the image processing unit so as to satisfy Conditional Expression (9) and Conditional Expression (11), and, when the control unit reduces the amount of the illumination light emitted from the light source unit, the control unit controls the image processing unit so as to satisfy Conditional Expression (10) and Conditional Expression (12):

$$Gr/Gg > 1 \quad (9)$$

$$Gr/Gg < 1 \quad (10)$$

$$Gb/Gg > 1 \quad (11)$$

$$Gb/Gg < 1 \quad (12)$$

where Gg is a gain by which a G signal in the image signal is multiplied, Gr is a gain by which an R signal in the image signal is multiplied, and Gb is a gain by which the B signal in the image signal is multiplied.

* * * * *